(12) United States Patent
Schwab et al.

(10) Patent No.: US 6,646,172 B1
(45) Date of Patent: Nov. 11, 2003

(54) PREPARATION OF PROPENE (75) Inventors: Peter Schwab, Bad Dürkheim (DE); Michael Schulz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/168,099

(22) Filed: Oct. 8, 1998

(30) Foreign Application Priority Data

Oct. 17, 1997 (DE) .......................... 197 46 040

(51) Int. Cl.[7] .............. C07C 6/04; C07C 6/00
(52) U.S. Cl. ............. 585/324; 585/313; 585/315; 585/316; 585/644; 585/646; 585/647
(58) Field of Search ................ 585/324, 313, 585/315, 316, 644, 646, 647

(56) References Cited

U.S. PATENT DOCUMENTS

| | | | |
|---|---|---|---|
| 3,526,676 A | | 9/1970 | Turner .......................... 260/683 |
| 3,767,565 A | | 10/1973 | Banks .......................... 208/44 |
| RE28,137 E | | 8/1974 | Turner .................... 260/683 D |
| 3,872,180 A | * | 3/1975 | Nakatomi et al. ....... 260/683 D |
| 3,915,897 A | * | 10/1975 | Reusser et al. .............. 252/457 |
| 4,187,362 A | * | 2/1980 | Hepworth et al. ............. 526/73 |
| 4,709,115 A | * | 11/1987 | Jung et al. ................... 585/643 |
| 5,304,615 A | * | 4/1994 | Ambler et al. .............. 526/189 |
| 5,321,191 A | * | 6/1994 | Alagy et al. ................ 585/648 |

FOREIGN PATENT DOCUMENTS

| | | |
|---|---|---|
| EP | 304 515 | 3/1989 |
| EP | 691 318 | 1/1996 |
| EP | 742234 | 11/1996 |
| EP | 832867 | 4/1998 |
| GB | 1054864 | * 6/1967 |

OTHER PUBLICATIONS

"Distillation Columns with Vertical Partitions"; Gerd Kaibel; Chem Eng Technol. 10 (1987) pp. 92–98, 1987.*
Hydrocarbon Processing, vol. 46, 1967, No. 11, 232, 55, 1976, No. 119–122.

* cited by examiner

Primary Examiner—Thuan D. Dang
(74) Attorney, Agent, or Firm—Keil & Weinkauf (57) ABSTRACT

A multistage process for preparing propene, in which the first stage is the reaction of 1-butene, 2-butene and isobutene to give propene, 2-pentene and 2-methyl-2-butene in the presence of a metathesis catalyst comprising at least one compound of a metal of transition group VIb, VIIb or VIII of the Periodic Table of the Elements; the second stage is separation of the propene and 2-pentene/2-methyl-2-butene formed; the third stage is reaction of the 2-pentene and 2-methyl-2-butene with ethehe to give propene, 1-butene and isobutene in the presence of a metathesis catalyst comprising at least one compound of a metal of transition group VIb, VIIb or VIII of the Periodic Table of the Elements; the fourth stage is separation of the propene and 1-butene/isobutene formed and returning the 1-butene and isobutene formed to the first stage.

11 Claims, 3 Drawing Sheets

PREPARATION OF PROPENE

The present invention relates to a process for preparing propene by metathesis of olefins. Olefin metathesis (disproportionation) in its simplest form describes the reversible, metal-catalyzed rearrangement of olefins by cleavage and reformation of C=C double bonds. For example, olefins of the formulae $R^1$—CH=CH—$R^2$ and $R^3$—CH=CH—$R^4$ are reversibly reacted to form olefins of the formulae $R^1$—CH=CH—$R^3$ and $R^2$—CH=CH—$R^4$. In the metathesis of acyclic olefins, a distinction is made between self-metathesis in which an olefin is converted into a mixture of two olefins having different molar masses and cross- or co-metathesis in which two different olefins react. An example of self-metathesis is the reaction of two molecules of propene to give ethene and 2-butene, as is performed, for example, by the Phillips triolefin process, see Hydrocarbon Processing, Volume 46, November 1967, No. 11, p. 232. An example of cross-metathesis is the reaction of propene and 1-butene to give ethene and 2-pentene. If one of the reactants is ethene, the reaction is customarily referred to as an ethenolysis.

The metathesis reactions are carried out in the presence of catalysts. Suitable catalysts for this purpose are, in principle, homogeneous and heterogeneous transition metal compounds, in particular those of transition groups VI to VIII of the Periodic Table of the Elements, as well as homogeneous and heterogeneous catalyst systems in which these compounds are present.

DE-A-19 40433 discloses the metathesis of 1-butene with 2-butene to form propene and 2-pentene, with $Re_2O_7/Al_2O_3$ being used as catalyst. The 2-pentene formed is reacted further with sodium hydride on potassium carbonate and ethene to give heptenes.

The metathesis of 1-butene and 2-butene to give propene and 2-pentene is mentioned in K. L. Anderson, T. D. Brown, Hydrocarbon Processing, Volume 55, August 1976, No. 8, pp. 119–122 as a secondary reaction in the synthesis of isoamylene.

EP-A-0 304 515 discloses a metathesis process for reacting 1-butene with 2-butene to give propene and pentenes, which is carried out in a reactive distillation apparatus using $Re_2O_7/Al_2O_3$ as catalyst.

U.S. Pat. No. 3,526,676 discloses the metathesis of 1-butene with 2-butene to give propene and pentene. It is carried out over $MoO_3$ and CoO on $AM_2O_3$.

U.S. Pat. No. 3,785,957 discloses a process for the production of fuel having a high octane number. In this process, an olefinic fuel is disproportionated together with ethylene and the product is fractionated into a propene stream, a butene stream, a $C_5$-or $C_5$–$C_6$-olefin stream and a $C_{6+}$ or $C_{7+}$ fuel stream. The $C_5$-or $C_5$–$C_6$-olefin stream is disproportionated with ethene over a $WO_3/SiO_2$ fixed-bed catalyst to give propene and butenes. The propene obtained is disproportionated to form ethene and butenes, and the butenes are alkylated with isobutane.

U.S. Pat. No. 3,767,565 discloses a process for increasing the octane number of fuel in which a $C_5$ fraction of an olefinic fuel is reacted with ethene in the presence of a catalyst comprising $WO_3/SiO_2$ and MgO to form ethene, propene, n-butenes and isobutenes. The propene obtained is disproportionated and the resulting n-butenes are alkylated with isobutane.

EP-A1-0 691 318 discloses an olefin metathesis process in which $C_5$-olefins and ethene are reacted in the presence of a catalyst to give mixed $C_4$-olefins and propene. Thus, 2-methyl-2-butene is reacted with ethene to give isobutene and propene. A mixture of 2-pentenes and 2-methyl-2-butene is reacted to give a mixture of 1-butene, isobutene and propene.

A process for preparing propene in high yield by reacting 1-butene, 2-butene and isobutene is not known.

A process for preparing propene in high yield without using an excess of ethene is not known. In the above processes, propene is prepared with addition of at least equimolar amounts of ethene. To achieve high propene selectivities, large amounts of ethene have to be circulated. In addition, isobutene present in the feed is not reacted and reduces the space-time yield.

It is an object of the present invention to provide a process for preparing propene in high yield from mixtures comprising 1-butene, 2-butene and isobutene. This should be able to be carried out without using an excess of ethene. It should be possible to obtain propene from $C_4$ streams which are low in 1-butene using very little ethene, and isobutene should also be converted into the desired product.

We have found that this objects is achieved by a process for preparing propene by reacting 1-butene, 2-butene and isobutene in the presence of a metathesis catalyst comprising at least one compound of a metal of transition group VIb, VIIb or VIII of the Periodic Table of the Elements, and subsequently separating off the propene.

We have also found that this object is achieved by a process for preparing propene by
a) reaction of 1-butene, 2-butene and isobutene to give propene, 2-pentene and 2-methyl-2-butene in the presence of a metathesis catalyst comprising at least one compound of a metal of transition group VIb, VIIb or VIII of the Periodic Table of the Elements,
b) subsequent separation of the propene and 2-pentene/2-methyl-2-butene formed,
c) subsequent reaction of the 2-pentene and 2-methyl-2-butene with ethene to give propene, 1-butene and isobutene in the presence of a metathesis catalyst comprising at least one compound of a metal of transition group VIb, VIIb or VIII of the Periodic Table of the Elements,
d) subsequent separation of the propene and 1-butene/isobutene formed,
e) subsequent return of the 1-butene and isobutene formed to step a).

The preferred process of the present invention comprises 2 metathesis steps. In the first step, 1-butene, 2-butene and isobutene are reacted to give propene, 2-pentene and 2-methyl-2-butene. In a second step, 2-pentene and 2-methyl-2-butene are then reacted with ethene to give 1-butene, isobutene and propene. According to one embodiment of the invention, 1-butene and isobutene are returned to the first reaction step.

The net reaction is thus the reaction of 2-butene with ethene to form 2 molecules of propene. According to one embodiment of the invention, the reaction of 2-pentene and 2-methyl-2-butene with ethene formally requires only equimolar amounts of starting materials in order to obtain the products in high yield. Thus, in contrast to the reverse trioolefin process, the amount of ethene used can be kept small.

Both metathesis steps can be carried out as a reactive distillation, as is described below.

According to one embodiment of the invention, 1-butene, 2-butene and isobutene can be used in the reaction as pure substances. According to another embodiment of the invention, the butenes are used in the form of a $C_4$ stream which originates, for example, from a cracker, in particular a stream cracker, or a refining process. This $C_4$ stream can comprise $C_4$-alkanes in addition to the butenes. According to an embodiment of the invention, use is made of a $C_4$ stream which consists of raffinate I. Raffinate I is here a fraction comprising 1-butene, cis/trans-2-butene, isobutene and also n-butane and iso-butane. For example, raffinate I can comprise 60–90% by weight of olefins and 10–40% by weight of butanes, with, for example, 10–40% by weight of 1-butene, 10–40% by weight of 2-butene and 10–50% by weight of isobutene. According to an embodiment of the invention, the $C_4$ stream used has a butene content of from 20 to 100% by weight, preferably from 50 to 90% by weight, in particular from 70 to 90% by weight. The ratio of 1-butene to 2-butene is from 10:1 to 1:10, preferably from 3:1 to 1:3, in particular 2:1 1:2. The molar ratio of 1-butene+2-butene to isobutene is preferably from 10:1 to 1:5, in particular from 3:1 to 1:2. According to one embodiment of the invention, the $C_4$ stream can contain small amounts of other hydrocarbons.

Raffinate I is preferably obtained by removal of butadiene from the crude $C_4$ fraction obtained in steam cracking. This is achieved either by butadiene extraction with polar aprotic solvents (e.g. N-methylpyrrolidone) or by selective hydrogenation. Depending on the work-up, different $C_4$ component distributions are obtained, for example (Figures in % by weight):

|  | after $C_4H_6$ extraction | after $C_4H_6$ selective hydrogenation |
| --- | --- | --- |
| 1-Butene | 26% | 33% |
| cis/trans-2-butene | 15% | 30% |
| i-Butene | 46% | 24% |
| Butadiene | 100 ppm | 2000 ppm |
| Butane | 13% | 13% |

In principle, both types of raffinate I are suitable for the process of the present invention.

According to an embodiment of the invention, the starting material used can be any stream in which 1-butene, 2-butene and isobutene are present. According to one embodiment of the invention, the 1-butene and isobutene can originate from the synthesis of the present invention itself and be mixed with introduced 2-butene.

The $C_4$ feed stream used is preferably pre-purified before use in the process of the present invention in order to remove any traces of water, oxygen or oxygenates, sulfur or sulfur-containing compounds, nitrogen, phosphorus or halogen, especially chlorides, which may be present. The removal is preferably carried out by passing the $C_4$ feed stream over adsorber material such as zeolites and zeolite-like phosphates, high-surface-area oxides of silicon, aluminum, titanium, zirconium, bleaching earths, clays, hydrotalcites, high-surface-area phosphates, activated carbons and carbon molecular sieves and also organic polymers and ion-exchange resins, preferably NaX molecular sieve. The adsorber materials are preferably present as a guard bed.

Methods which can be used for adsorption and adsorptive purification are described, for example, in W. Kast, Adsorption aus der Gasphase, VCH, Weinheim (1988). The use of zeolitic adsorbents is explained in D. W. Breck, Zeolite Molecular Sieves, Wiley, N.Y. (1974). The removal of, specifically, acetaldehyde from $C_3$–$C_{15}$-hydrocarbons in the liquid phase is described in EP-A-0 582 901. The methods described in the above references can be used here. Thus, the feed stream in gaseous, liquid or supercritical phase is preferably brought into contact with the adsorbents.

Apart from the reaction of 1-butene, 2-butene and isobutene to form propene and 2-pentene and also 2-methyl-2-butene, a small proportion of 3-hexene, ethene, 2,3-dimethyl-2-butene and 2-methyl-2-pentene can be obtained as by-product. In addition, small amounts of higher-boiling compounds can also be present:

In the above reaction, the desired molecular propene is formed in a cross-metathesis reaction of the á-olefins 1-butene and i-butene with 2-butene. Approximately equimolar amounts of the $C_5$-olefins 2-pentene and 2-methyl-2-butene are obtained as coproducts. Signficantly less favored are the respective self-metathesis reactions of 1-butene and isobutene (to form ethene and 3-hexene or 2,3-dimethyl-2-butene) and the cross-metathesis of the two á-olefins (to form 2-methyl-2-pentene). The formation of the isobutene self-metathesis product 2,3-dimethyl-2-butene was not observed.

The $C_4^+$-olefins obtained in this first step can, after removal of ethene and propene by distillation, function as co-cracking feed with a significantly higher cracking value than the starting material. As an alternative, after separation of $C_4$ and $C_5^+$, the propene yield can be increased by the ethenolysis of $C_5^+$ described below. Secondary components obtained in this reaction are preferably exclusively 1-butene and i-butene which can be recirculated to the first metathesis step or alternatively be isolated as pure materials using known technology.

3-Hexen + 2-Methyl-2-penten i-Buten

The small amounts of by-products in the first step, which according to an embodiment of the invention make up from 1 to 20% by weight, preferably from 1 to 5% by weight, of the amount of 2-pentene and 2-methyl-2-butene formed, do not interfere in the subsequent reaction (ethenolysis) so that, according to one embodiment of the invention, no purification of the 2-pentene and 2-methyl-2-butene to remove these by-products is necessary before the further reaction. According to one embodiment of the invention, the 2-pentene and 2-methyl-2-butene are used in pure form in the secondary reaction.

The expression "2-pentene and 2-methyl-2-butene" also includes those mixtures comprising not only 2-pentene and 2-methyl-2-butene but also small amounts of hexenes, in particular 3-hexene, and other higher-boiling compounds.

Correspondingly, the expression "butenes", like "1-butene", "2-butene" and "isobutene", also includes a mixture which comprises not only the butene or butenes but also $C_4$-alkanes, in particular butanes.

A number of embodiments of the invention are illustrated below with the aid of the drawing, in which FIG. 1 schematically shows an embodiment of the process of the invention

The abbreviations employed in the figures have the following meanings:

Bu: butanes
Et: ethene
Pr: propene
H: high boilers
I: raffinate I
C4: C4 olefins
C5+: olefins having 5 or more carbon atoms
R1: reactor
R2: reactor
D1: distillation column (if a vertical line is shown under D1, the column is a dividing wall column)
D2: column (if a vertical line is shown under D2, the column is a dividing wall column)
D3: distillation column Described below is one embodiment of the process of the invention, comprising a) reaction of 1-butene, 2-butene and isobutene to give propene, 2-pentene and 2-methyl-2-butene in the presence of a metathesis catalyst comprising at least one compound of a metal of transition group VIb, VIIb or VIII of the Periodic Table of the Elements, b) subsequent separation of the propene and 2-pentene/2-methyl-2-butene formed, c) subsequent reaction of the 2-pentene and 2-methyl-2-butene with ethene to give propene, 1-butene and isobutene in the presence of a metathesis catalyst comprising at least one compound of a metal of transition group VIb, VIb or VIII of the Periodic Table of the Elements, d) subsequent separation of the propene and 1-butene/isobutene formed, e) subsequent return of the 1-butene and isobutene formed to step a).

Figure 1:
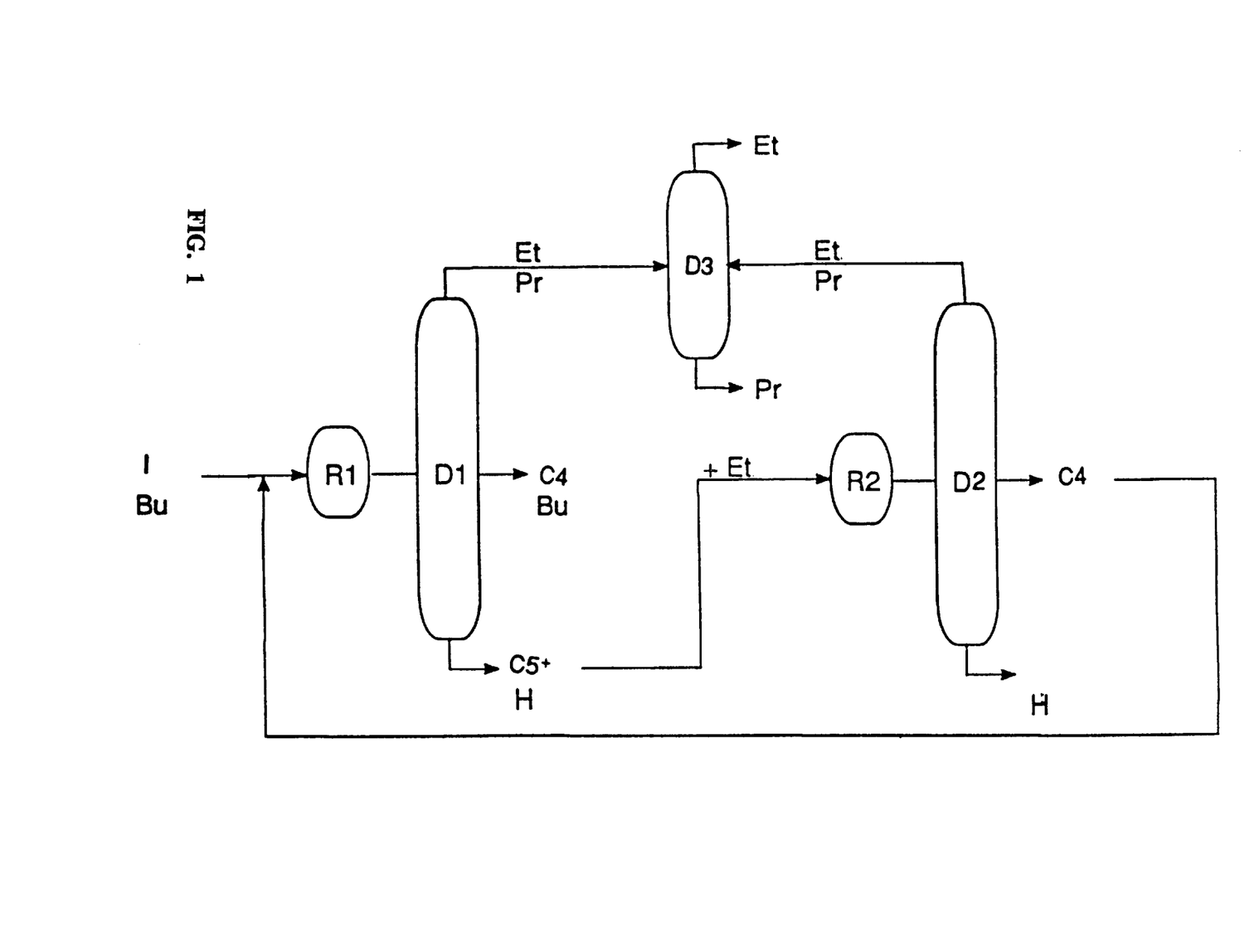

This embodiment is shown in FIG. 1.

In a first reactor R1, 1-butene, 2-butene and isobutene are reacted in the presence of the metathesis catalyst of the present invention to give propene, 2-pentene and 2-methyl-2-butene. For this purpose, a raffinate I stream is fed to the reactor. The reactor is followed by a distillation column D1 at the top of which propene and ethene formed as by-product are removed. Unreacted raffinate I is taken off at the middle offtake. Some of it may: also be returned to the reactor R1 (not shown in FIG. 1). 2-Pentene, 2-methyl-2-butene and 3-hexene formed as by-product as well as high boilers are taken off at the bottom of D1. The bottoms are then fed together with added ethene to a reactor R2 which again contains a metathesis catalyst of the present invention. In this reactor R2, the reaction of 2-pentene and 2-methyl-2-butene with ethene to give 1-butene, isobutene and propene takes place. The reaction product from reactor R2 is fed to a distillation column D2 at the top of which propene and unreacted ethene are taken off. 1-Butene and isobutene formed are taken off at the middle offtake and at least sore is preferably returned to the reactor R1. Unreacted 2-pentene, 2-methyl-2-butene and also, as by-products, 3-hexene and high boilers are obtained at the bottom of D2. These are preferably returned to the reactor R2. The mixtures of propene and by-product ethene taken off at the top of D1 and D2 are fractionated in a further distillation column D3. Ethene is obtained at the top of D3 and this is preferably returned to the reactor R2 (not shown in FIG. 1), or discharged as co-cracker feed. The propene obtained at the bottom of D3 is the desired reaction product of the process of the present invention. D1 and D2 are designed such that a low-boiling phase, in particular a $C_{2/3}$ phase comprising ethene and propene, is taken off at the top of the column. $C_4$ streams, in particular butenes and butanes, are taken off as intermediate-boiling phase. As bottoms, $C_{\geq 5}$-hydrocarbons are discharged.

The reactors R1 and R2 can be any suitable reactors. They can serve for continuous or batchwise operation. Thus, according to one embodiment, they can be pressure vessels such as glass pressure vessels, while according to a further embodiment they can be tube reactors.

According to an embodiment of the invention, the total conversion in R1 is from 20 to 90%, preferably from 50 to 80%.

According to an embodiment of the invention, the total conversion in R2 is from 20 to 100%, preferably from 60 to 90%.

The reaction in R1 preferably takes place in the liquid phase. Here, pressure and temperature are selected such that the reactants remain in the liquid phase.

According to an embodiment of the invention, the temperature in R1 is from 0 to 150° C., preferably from 20 to 80°

C. According to an embodiment of the invention, the pressure is from 2 to 200 bar, preferably from 5 to 20 bar. The reaction in R2 (ethenolysis) is, according to an embodiment of the invention, carried out at from 20 to 150° C., preferably from 20 to 80° C., under an ethene pressure of from 5 to 200 bar, preferably from 30 to 80 bar. Further ethene can be injected continuously so that a constant pressure is maintained.

The reactions in R1 and R2 can be carried out continuously or batchwise in reactors such as (glass) pressure vessels, tube reactors or reaction columns for a time of from one second to ten hours, preferably from 1 to 60 minutes. Preference is given to using tube reactors.

The distillation columns D1 and D2 are, according to an embodiment of the invention, columns which allow separation of a hydrocarbon stream into $C_{2/3}$ streams, $C_4$ streams and $C_{\geq 5}$ streams. The columns can be designed as dividing wall columns. According to an embodiment of the invention, D3 is a column which allows the separation of ethene and propene. According to one embodiment of the invention, the reactor R1 is combined with the distillation column D1 to form a reactive distillation apparatus. Here, the reaction is carried out directly in the distillation column. The catalyst is present in the reaction column so that the distillation is carried out simultaneously with the reaction or immediately thereafter. A corresponding process is known under the name "reactive distillation".

According to one embodiment, reactor R2 and distillation column D2 are combined to form a reactive distillation apparatus in which the reaction and distillation are combined as in the above-described reactive distillation.

According to one embodiment of the invention, both reactions take place in reactive distillation apparatuses. Both reactions are equilibrium reactions so that, according to one embodiment of the invention, the process products are removed as quickly as possible from the equilibrium to achieve as high as possible a conversion. This is possible, in particular, when using reactive distillation apparatuses.

Figure 2:
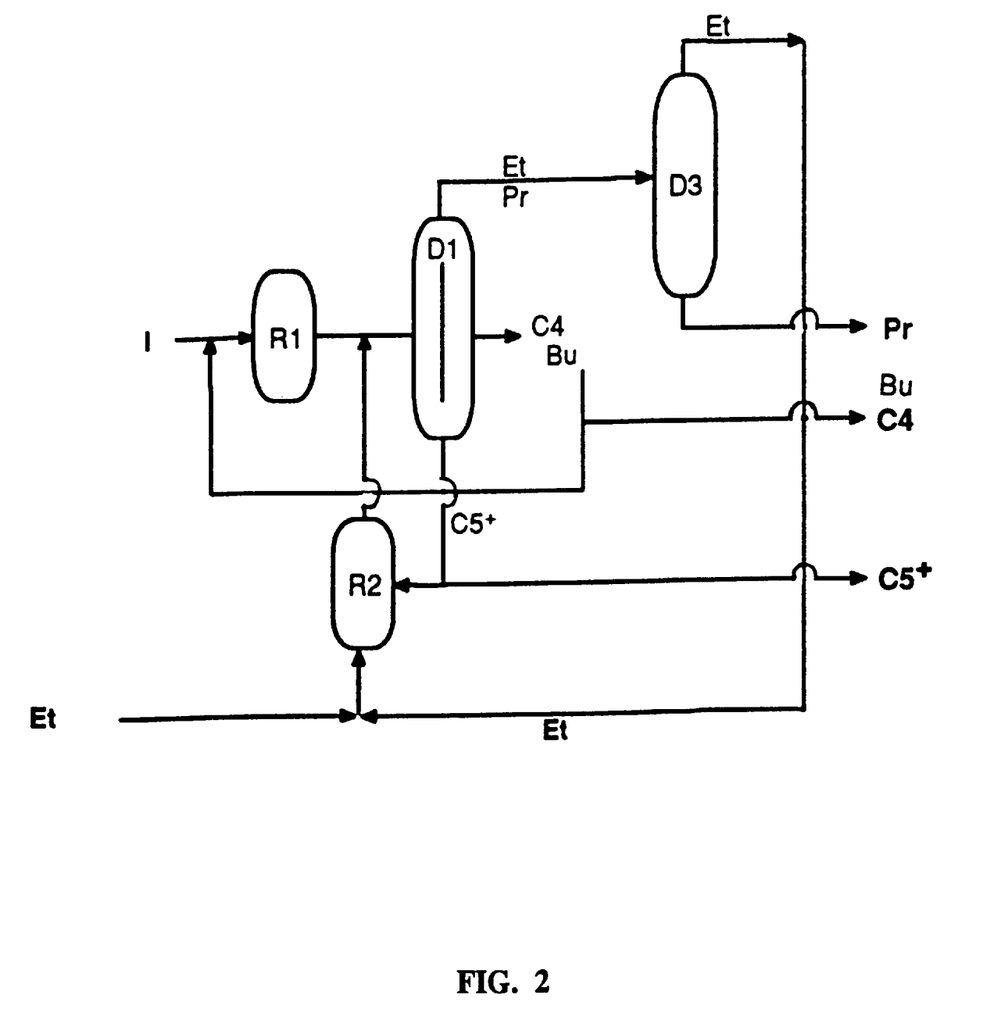
FIG. 2 shows a further embodiment of the process of the invention.

In place of a normal distillation column DI, a dividing wall column can be provided. Such a process is shown in FIG. 2. The process shown is additionally modified compared with that shown in FIG. 1.

As in the above-described embodiment, a metathesis is carried out over a heterogeneous metathesis catalyst in the reactor R1, using raffinate I. The distillation column D1 serves to separate the reaction products formed in the metathesis. The distillation column D3 serves to separate ethene and propene. The reactor R2 is for the reaction of $C_5^+$ high boilers with ethene. Unlike the previous embodiment, the distillation column D1 is configured as a dividing wall column. In addition, some of the intermediate-boiling product from D1, which comprises $C_4$ olefins and butanes, is returned to the raffinate I feed stream. Since the distillation columns D1 and D2 have to perform the same separation task, only one such distillation column D1 is provided in this embodiment. This allows the outlay in terms of apparatus to be reduced. The reaction scheme was adapted correspondingly: the high-boiling product from D1 is fed to the reactor R2 or some of it is discharged. The output from the reactor R2 is fed to the distillation column D1. Part of the ethene feed to the reactor R2 is from the low-boiling product from the distillation column D3 and the other part is additional ethene fed in. The output from the process consists of propene as main product and in addition $C_4$ olefins and $C_5^+$ olefins.

Figure 3:
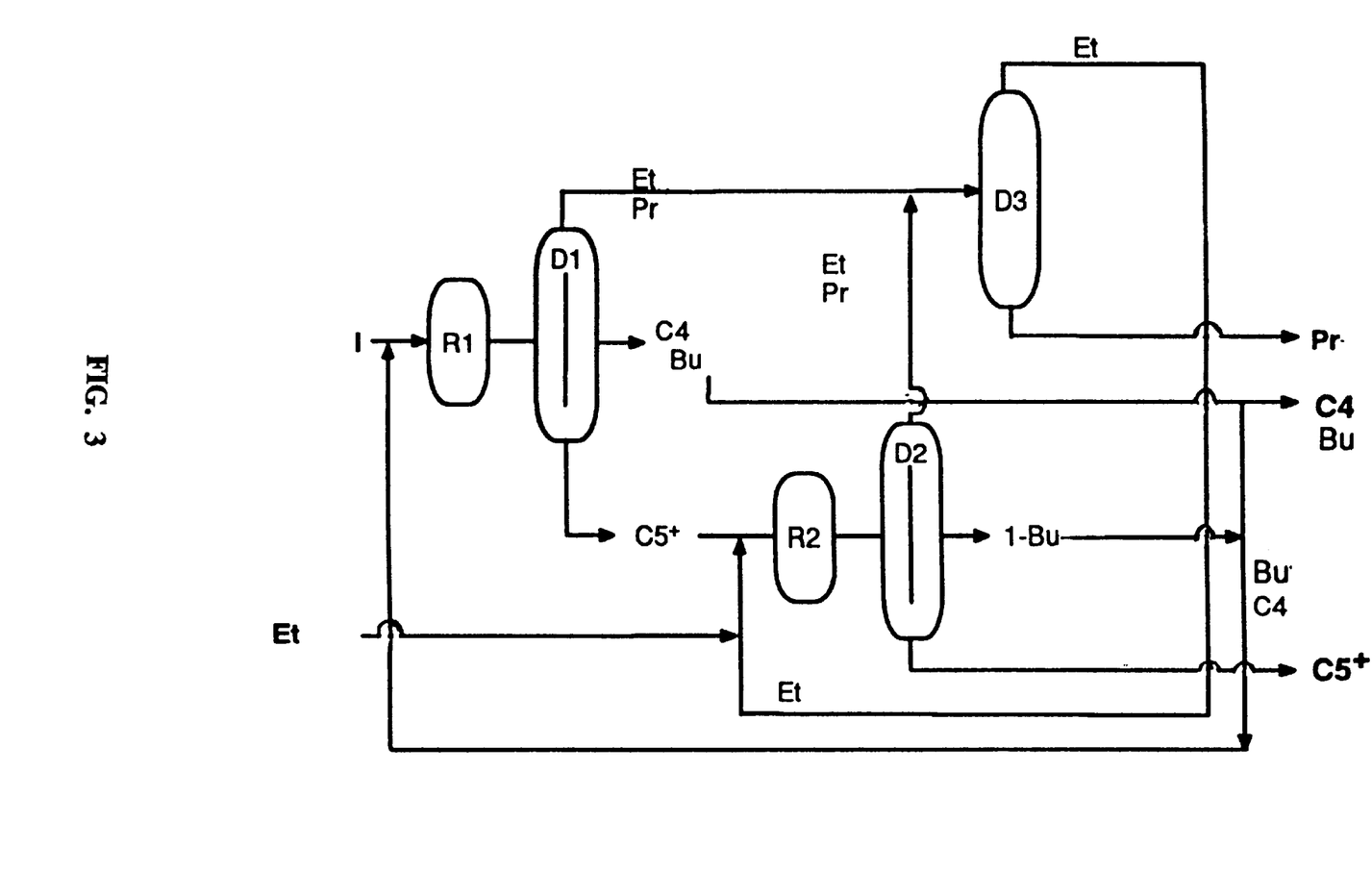
FIG. 3 shows a further embodiment of the process of the invention.

FIG. 3 shows an embodiment of the process of the present invention which largely corresponds to the embodiment shown in FIG. 1. The column D2 is, like the column D1, configured as a dividing wall column.

Unlike the process shown in FIG. 1, some of the intermediate-boiling product from D1, which comprises $C_4$ olefins and butanes, is discharged and some of it is combined with the intermediate-boiling product from the column D2 and returned to the reactor R1. The ethene obtained from the distillation column D3 is fed to the reactor R2 in which the reaction with the $C_5^+$ fraction takes place. Again, propene as main product and parts of the $C_4$ olefin fraction and butanes and also the $C_5^+$ fraction from the distillation column D2 (also as co-cracker feed) are discharged.

Catalyst

All suitable metathesis catalysts can be used in the process of the present invention. According to an embodiment of the invention, the catalyst is a heterogeneous catalyst, in particular a supported catalyst. According to an embodiment of the invention, the catalyst comprises at least one compound of a metal of transition group VIb, VIIb or VIII of the Periodic Table of the Elements. The catalyst preferably comprises a ruthenium compound and/or rhenium compound. Such catalysts are described, for example, in K. J. Ivin, I. C. Mol, Olefin Metathesis and Metathesis Polymerization, 2nd edition, Academic Press, New York; 1996; G. W. Parshall, S. D. Ittel, Homogeneous Catalysis, 2nd edition, 1992, John Wiley & Sons, New York, Chichester, Brisbane, Toronto, Singapore, p. 217 ff; R. H. Grubbs in Prog. Inorg. Chem., S. Lippard (Editor), John Wiley & Sons, New York, 1978, Vol. 24, 1–50; R. H. Grubbs in Comprehensive Organomet. Chemie., G. Wilkinson (Editor), Pergamon Press, Ltd., New York, 1982, Vol. 8, 499–551; D. S. Breslow, Prog. Polym. Sci. 1993, Vol. 18, 1141–1195.

According to one embodiment of the invention, the metal compound is a metal oxide, partial oxide with additional organic radicals or a carbonyl compound.

According to one embodiment of the invention, a homogeneous catalyst is used. The catalyst is here at least one compound of a metal of transition group VIb, VIb or VIII of the Periodic Table of the Elements. Preference is given to using rhenium or ruthenium in the metal compounds.

According to one embodiment of the invention, use is made of ruthenium compounds as are described in WO 93/20111 and WO 96/04289 and also J. Chem. Soc., Chem. Commun. 1995, 1127 to 1128.

According to a preferred embodiment of the invention, use is made of $RuX_2(CHR)(PR'_3)_2$, where the radicals R and R' are $C_1$–$C_{12}$-alkyl radicals, preferably $C_1$–$C_6$-alkyl radicals, or $C_6$–$C_{12}$-aryl radicals, $R^1$ is particularly preferably a $C_3$–$C_8$-cycloalkyl radical, in particular a $C_5$- or $C_6$-cycloalkyl radical, and X is a halide such as chloride, bromide or iodide.

In particular, $RuCl_2(=CHPh)(PCy_3)_2$ is used according to the present invention, according to one embodiment of the invention as solution, for example in methylene chloride.

The metal compound is preferably an oxide of molybdenum, tungsten or, preferably, rhenium, in particular $Re_2O_7$.

Support

According to an embodiment of the invention, the catalysts of the present invention comprise a support. Supports employed here are, in particular, inorganic supports such as $Al_2O_3$, in particular a-$Al_2O_3$, $SiO_2$, $Fe_2O_3$, or mixtures thereof such as $SiO_2/Al_2O_3$, $B_2O_3/SiO_2/Al_2O_3$ or $Fe_2O_3/Al_2O_3$.

The metal oxide content on the support is, according to one embodiment of the invention, from 1 to 20% by weight, preferably from 3 to 15% by weight, in particular from 8 to 12% by weight, based on the total weight of the supported catalyst.

Use can be made, for example, of $Re_2O_7$ on $Al_2O_3$, a catalyst which is active even under very mild reaction conditions of from 20 to 80° C., or $MO_3/SiO_2$, where M is Mo or W, at a relatively high reaction temperature.

The catalyst used is preferably $Re_2O_7$ on $Al_2O_3$, $SiO_2/Al_2O_3$, $SiO_2/Al_2O_3$ $Fe_2O_3$ or $B_2O_3/Al_2O_3$. The proportion of metal oxide here is preferably from 1 to 20% by weight, particularly preferably from 3 to 10% by weight. According to one embodiment of the invention, $MeReO_3$ is used in place of $Re_2O_7$ or in admixture therewith.

According to the present invention, particular preference is given to using $Re_2O_7$ on $Al_2O_3$.

According to one embodiment of the invention, the catalysts are used in freshly calcined form and then require no further activation, for example by means of alkylating agents. Deactivated catalysts can, according to the present invention, be regenerated by burning off carbon residues, for example at 550° C. in a stream of air and cooling under argon.

The reactions of the present invention can be carried out in the presence of a solvent, for example a hydrocarbon solvent. According to a preferred embodiment of the invention, the reactions are carried out without further added solvent.

EXAMPLES

Continuous experiments on the synthesis of propene from raffinate 1.

Examples 1 to 3

Continuous experiments on the metathesis of i-butene-containing $C_4$ fractions: raffinate I was passed continuously at 60° C. and 10 bar at different residence times through a tube reactor charged with a heterogeneous $Re_2O_7/Al_2O_3$ catalyst. The reaction product was, after depressurization, analyzed by gas chromatography. The results are shown in Table 1.

TABLE 1

| Example | Res. t. (min) | Conversion of 1-butene | conversion of i-butene | conversion of 2-butene | total conversion of butenes | STY of propene |
|---|---|---|---|---|---|---|
| 1 | 10 min | 65% | 39% | 42% | 49% | 550 g/l-h |
| 2 | 5 min | 65% | 39% | 46% | 50% | 970 g/l-h |
| 3 | 3 min | 58% | 30% | 40% | 43% | 1200 g/l-h |

STY: space-time yield
Res. t.: residence time

Examples 4 to 5

Continuous experiments on the ethenolysis of the $C_5/C_6$ high boiler product: the high boiler product obtained in Examples 1 to 3, comprising 2-pentene, 2-methyl-2-butene, 3-hexene and 2-methyl-2-pentene, was passed continuously at 60° C. and 50 or 70 bar of ethene (feed stock ratio $C_2:C_5$, $C_6$=1:1) through a tube reactor charged with heterogeneous $Re_2O_7/Al_2O_3$ catalyst. The reaction product was, after depressurization, analyzed by gas chromatography. The results are shown in Table 2.

TABLE 2

| Example | Conversion of 2-pentene | Conversion 2-Mc-2-butene | Conversion of 3-Hexen | Conversion of 2-Mc-Pentene | Selectivity of propene |
|---|---|---|---|---|---|
| 4 | 89% | 83% | 87% | 85% | 91% |
| 5 | 92% | 85% | 90% | 88% | 93% |

We claim:
1. A process for preparing propene by
   a) reaction of a mixture containing 1-butene, 2-butene and isobutene to give a product mixture containing propene, 2-pentene and 2-methyl-2-butene in the presence of a metathesis catalyst comprising at least one compound of a metal of transition group VIb, VIIb or VIII of the Periodic Table of the Elements,
   b) subsequent separation by distillation of the product mixture formed in a), into low boiling $C_{2-3}$ hydrocarbons, intermediate $C_4$ hydrocarbons and a mixture of 2-pentene and 2-methyl-2-butene or a mixture of 2-pentene, 2-methyl-2-butene and small amounts of higher boiling compounds,
   c) subsequent reaction of said mixture of 2-pentene and 2-methyl-2-butene or said mixture containing 2-pentene, 2-methyl-2-butene and small amounts of higher boiling compounds from b, with ethene to give a mixture containing propene, 1-butene and isobutene, or propene, 1-butene, isobutene and butanes, in the presence of a metathesis catalyst comprising at least one compound of a metal of transition group VIb, VIIb or VIII of the Periodic Table of the Elements an excess of ethene in not uncut,
   d) subsequent separation by distillation of the mixture formed in step c into low boiling $C_{2-3}$ hydrocarbons, a mixture of 1-butene and isobutene or mixture of 1-butene, isobutene and butanes, and $C_{\geq 5}$-hydrocarbons,
   e) subsequent return of the mixture of 1-butene and isobutene or mixture of 1-butene, isobutene and butanes resulting from step d) to step a).

2. A process as claimed in claim 1, wherein the reaction in steps a) and/or c) is not carried to completion and in step b) and/or d) wherein either or both of said low-boiling hydrocarbons either separately or combined, are separated by distillation into $C_2$ and $C_3$ phases and the $C_2$ phase is returned to step c),
   at least some of said intermediate-boiling hydrocarbons, either separately or combined, are returned to step a) and at least some of said bottom hydrocarbons either separately or combined, are returned to step c).

3. A process as claimed in claim 1, wherein said reaction mixture containing 1-butene, 2-butene and isobutene is a $C_4$ stream from a cracker or refining process.

4. A process as claimed in claim 3, wherein the molar ratio of 1-butene to 2-butene is from 10:1 to 1:10 and the molar ratio of 1-butene+2-butene to isobutene is from 10:1 to 1:5.

5. A process as claimed in claim 3, wherein said $C_4$ stream is pre-purified by passage over adsorber materials.

6. A process as claimed in claim 1, wherein said metathesis catalyst is a homogeneous or hetero-geneous metathesis catalyst comprising a rhenium or ruthenium compound.

7. A process as claimed in claim 6, wherein said metathesis catalyst comprises or consists of $Re_2O_7$ on an $Al_2O_3$ support, with the rhenium oxide content being from 1 to 20% by weight, based on the total weight of the catalyst.

8. A process as claimed in claim 1, wherein step a) or step c) or both steps a) and c) are carried out as a reactive distillation.

9. A process as claimed in claim 1, wherein either or both of steps b) and d) are carried out in a distillation column.

10. A process as claimed in claim 9, wherein said distillation column is a dividing wall column in which, when used in step b), a propene-containing low-boiling phase, optionally a butene-containing intermediate-boiling phase and a 2-pentene- and 2-methyl-2-butene-containing bottom phase are obtained, and when used in step d), a propene-containing low-boiling phase, a 1-butene- and isobutene-containing intermediate-boiling phase and optionally a 2-pentene- and 2-methyl-2-butene-containing bottom phase are obtained.

11. A process as claimed in claim 1, wherein ethene is separated from the low boiling $C_{2-3}$ hydrocarbons from either step b) or step d) or both and returned to step c).

* * * * *

UNITED STATES PATENT AND TRADEMARK OFFICE
CERTIFICATE OF CORRECTION

PATENT NO.     : 6,646,172 B1                                              Page 1 of 1
DATED          : November 11, 2003
INVENTOR(S)    : Schwab et al.

It is certified that error appears in the above-identified patent and that said Letters Patent is hereby corrected as shown below:

<u>Title page,</u>
Item [57], ABSTRACT,
Line 9, "ethehe" should be -- ethene --.

<u>Column 10,</u>
Line 35, "uncut" should be -- used --.
Line 64, "hetero-geneous" should be -- heterogeneous --.

Signed and Sealed this

Tenth Day of February, 2004

JON W. DUDAS
*Acting Director of the United States Patent and Trademark Office*